(12) United States Patent
Marsh et al.

(10) Patent No.: US 10,111,815 B2
(45) Date of Patent: *Oct. 30, 2018

(54) COMPOSITION FOR HAIR FRIZZ REDUCTION

(71) Applicant: The Procter & Gamble Company, Cincinnati, OH (US)

(72) Inventors: Jennifer Mary Marsh, Deerfield Township, OH (US); Supriya Punyani, Singapore (SG); Stevan David Jones, Singapore (SG); Michael Lee Vatter, Okeana, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/742,136

(22) Filed: Jun. 17, 2015

(65) Prior Publication Data

US 2015/0359716 A1 Dec. 17, 2015

Related U.S. Application Data

(60) Provisional application No. 62/013,163, filed on Jun. 17, 2014.

(51) Int. Cl.
*A61K 8/46* (2006.01)
*A61K 8/365* (2006.01)
*A61Q 5/00* (2006.01)
*A61K 8/368* (2006.01)
*A61K 8/36* (2006.01)
*A61K 8/34* (2006.01)
*A61K 8/89* (2006.01)
*A61K 8/42* (2006.01)
*A61Q 5/06* (2006.01)

(52) U.S. Cl.
CPC ............ *A61K 8/368* (2013.01); *A61K 8/345* (2013.01); *A61K 8/36* (2013.01); *A61K 8/365* (2013.01); *A61K 8/42* (2013.01); *A61K 8/466* (2013.01); *A61K 8/89* (2013.01); *A61Q 5/06* (2013.01); *A61K 2800/58* (2013.01)

(58) Field of Classification Search
None
See application file for complete search history.

(56) References Cited

U.S. PATENT DOCUMENTS

| | | |
|---|---|---|
| 2,392,314 A | 1/1946 | Dalton |
| 4,496,536 A | 1/1985 | Moller et al. |
| 4,678,475 A | 7/1987 | Hoshowski et al. |
| 5,102,655 A | 4/1992 | Yoshihara et al. |
| 5,384,114 A | 1/1995 | Dowell et al. |
| 5,587,155 A | 12/1996 | Ochiai et al. |
| 5,688,495 A | 11/1997 | Rosen et al. |
| 6,001,340 A | 12/1999 | Rosen et al. |
| 6,156,299 A | 12/2000 | Rosen et al. |
| 6,294,186 B1 | 9/2001 | Beerse et al. |
| 6,495,498 B2 | 12/2002 | Niemiec et al. |
| 6,858,202 B2 | 2/2005 | Niemiec et al. |
| 6,908,889 B2 | 6/2005 | Niemiec et al. |
| 7,527,654 B2 | 5/2009 | Plos |

(Continued)

FOREIGN PATENT DOCUMENTS

| | | |
|---|---|---|
| DE | 19536423 A1 | 4/1996 |
| DE | 102011089357 A1 | 8/2012 |

(Continued)

OTHER PUBLICATIONS

Special Chem ([retrieved from on-line website http://cosmetics.specialchem.com/inci/hydroxyethyl-urea, last visit Sep. 14, 2016]).*
JP2008-20871A English translation provided by EPO. (Year: 2008).*
"Infusion 23 (Colour) Ologie Leave-In Treatment", Procter & Gamble, Feb. 1, 2007, Mintel.
"De-Frizz Leave-In Treatment", Quality Collor Cosmeticos, May 1, 2014, Mintel.
PCT Invitation to Pay Additional Fees and, Where Applicable, Protest Fee for PCT/US2015/036195, dated Oct. 7, 2015.
Invitation to Pay Additional Fees and, Where Applicable, Protest Fee for PCT/US2015/036192 dated Jan. 4, 2016.

(Continued)

*Primary Examiner* — Ernst V Arnold
*Assistant Examiner* — Kyung S Chang
(74) *Attorney, Agent, or Firm* — Linda M. Sivik

(57) ABSTRACT

A composition directed to an aqueous hair leave-on composition for hair frizz reduction comprising from about 0.15% to about 12.0% of a moisture control material or mixture of moisture control materials wherein the moisture control material is selected from one or more of the following class:

Class I having the structure selected from:

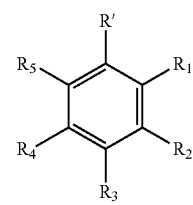

wherein R' is —COOY, sulfonic acid, or C=CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH=CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0.

15 Claims, No Drawings

(56) References Cited

U.S. PATENT DOCUMENTS

| | | |
|---|---|---|
| 8,512,686 B2 | 8/2013 | Morioka |
| 8,968,712 B2 | 3/2015 | Tanaka |
| 9,095,528 B2 | 8/2015 | Desenne et al. |
| 9,216,146 B2 | 12/2015 | Tanaka |
| 9,259,070 B2 | 2/2016 | Fischer et al. |
| 9,265,321 B2 | 2/2016 | Fischer et al. |
| 9,271,908 B2 | 3/2016 | Allef et al. |
| 2003/0022936 A1 | 1/2003 | Milbradt et al. |
| 2003/0143173 A1 | 7/2003 | Buck |
| 2003/0215405 A1 | 11/2003 | Parker et al. |
| 2003/0223952 A1 | 12/2003 | Wells et al. |
| 2004/0120911 A1 | 6/2004 | Shah et al. |
| 2004/0180016 A1 | 9/2004 | Buck |
| 2004/0261198 A1 | 12/2004 | Kainz et al. |
| 2005/0136015 A1 | 6/2005 | McKie et al. |
| 2005/0143268 A1 | 6/2005 | Midha et al. |
| 2005/0169869 A1 | 8/2005 | Laurent et al. |
| 2005/0175567 A1 | 8/2005 | Khoshdel et al. |
| 2005/0196369 A1 | 9/2005 | Ueyama et al. |
| 2005/0266034 A1 | 12/2005 | Muller et al. |
| 2006/0165636 A1 | 7/2006 | Hasebe et al. |
| 2006/0204466 A1 | 9/2006 | Littau et al. |
| 2006/0286059 A1 | 12/2006 | Yang et al. |
| 2007/0104667 A1 | 5/2007 | Mondet et al. |
| 2007/0149423 A1 | 6/2007 | Warr et al. |
| 2007/0261179 A1 | 11/2007 | Dorkel et al. |
| 2008/0138438 A1 | 6/2008 | Taylor et al. |
| 2008/0194454 A1 | 8/2008 | Morgan et al. |
| 2009/0169502 A1 | 7/2009 | Quadir |
| 2009/0324531 A1 | 12/2009 | Okada et al. |
| 2010/0297051 A1 | 11/2010 | Feuillette |
| 2010/0300472 A1 | 12/2010 | Malle et al. |
| 2010/0330007 A1 | 12/2010 | Spindler et al. |
| 2011/0003016 A1 | 1/2011 | Burry et al. |
| 2011/0269658 A1 | 11/2011 | Dihora et al. |
| 2012/0070398 A1 | 3/2012 | Nagano et al. |
| 2012/0093751 A1 | 4/2012 | Nagano et al. |
| 2012/0308506 A1 | 12/2012 | Oku et al. |
| 2013/0064908 A1 | 3/2013 | Noh |
| 2013/0125915 A1 | 5/2013 | Nagase et al. |
| 2013/0164390 A1 | 6/2013 | Richards et al. |
| 2013/0259817 A1 | 10/2013 | Uehara et al. |
| 2013/0259819 A1 | 10/2013 | Uehara et al. |
| 2013/0306095 A1 | 11/2013 | Syed |
| 2014/0079660 A1 | 3/2014 | Doi |
| 2014/0154197 A1 | 6/2014 | Swaile et al. |
| 2014/0179645 A1 | 6/2014 | Arndt |
| 2015/0174052 A1 | 6/2015 | Mette et al. |
| 2015/0313832 A1 | 11/2015 | Hilvert et al. |
| 2015/0359716 A1 | 12/2015 | Marsh et al. |
| 2016/0015608 A1 | 1/2016 | Marsh et al. |
| 2016/0022558 A1 | 1/2016 | Kunin et al. |
| 2016/0158128 A1 | 6/2016 | Marsh et al. |
| 2016/0158135 A1 | 6/2016 | Marsh et al. |
| 2016/0175209 A1 | 6/2016 | Walker et al. |
| 2016/0228342 A1 | 8/2016 | Rose |
| 2016/0287494 A1 | 10/2016 | Punyani et al. |
| 2016/0287495 A1 | 10/2016 | Punyani et al. |
| 2017/0216172 A1 | 8/2017 | Carballada et al. |
| 2017/0290755 A1 | 10/2017 | Soh et al. |

FOREIGN PATENT DOCUMENTS

| | | |
|---|---|---|
| EP | 1787680 A2 | 5/2007 |
| EP | 1326577 B1 | 10/2008 |
| EP | 2036536 A1 | 3/2009 |
| EP | 2392314 A1 | 12/2011 |
| FR | 2931659 B1 | 3/2011 |
| FR | 2968946 B1 | 4/2013 |
| GB | 816750 | 7/1959 |
| JP | S63156711 A | 6/1988 |
| JP | H06256137 A | 9/1994 |
| JP | 3009959 B2 | 2/2000 |
| JP | 3026213 B2 | 3/2000 |
| JP | 2001-122737 A | 5/2001 |
| JP | 2001122737 A | 5/2001 |
| JP | 2005145883 A | 6/2005 |
| JP | 2005-194261 A | 7/2005 |
| JP | 2005194261 A | 7/2005 |
| JP | 3843051 B2 | 11/2006 |
| JP | 2007-070469 A | 3/2007 |
| JP | 2008208071 A * | 9/2008 |
| JP | 4329097 B2 | 9/2009 |
| JP | 4452523 B2 | 4/2010 |
| JP | 4625357 B2 | 2/2011 |
| JP | 4679893 B2 | 5/2011 |
| JP | 4883261 B2 | 2/2012 |
| JP | 5086539 B2 | 11/2012 |
| JP | 5228338 B2 | 7/2013 |
| JP | 2014097931 A | 5/2014 |
| JP | 5779399 B2 | 9/2015 |
| WO | 01/28338 A2 | 4/2001 |
| WO | 01/28339 A2 | 4/2001 |
| WO | WO2011074134 A1 | 6/2011 |
| WO | WO2012131848 A1 | 10/2012 |
| WO | WO 2014/002668 A1 | 1/2014 |
| WO | WO 2014/100970 A1 | 7/2014 |
| WO | WO2014100970 A1 | 7/2014 |

OTHER PUBLICATIONS

Invitation to Pay Additional Fees and, Where Applicable, Protest Fee for PCT/US2015/063893, dated Feb. 8, 2016.
U.S. Appl. No. 14/959,243, filed Dec. 4, 2015, Song et al.
U.S. Appl. No. 14/959,234, filed Dec. 4, 2015, Song et al.
U.S. Appl. No. 14/677,636, filed Apr. 2, 2015, Punyani et al.
U.S. Appl. No. 14/677,578, filed Apr. 2, 2015, Punyani et al.
PCT International Search Report and Written Opinion for PCT/US2015/036192 dated Mar. 21, 2016.
PCT Invitation to Pay Additional Fees and, Where Applicable, Protest Fee for PCT/US2015/063888 dated Mar. 9, 2016.
U.S. Appl. No. 15/367,356, filed Dec. 2, 2016, Punyani et al.
U.S. Appl. No. 15/367,363, filed Dec. 2, 2016, Punyani et al.
U.S. Appl. No. 15/367,369, filed Dec. 2, 2016, Punyani et al.
U.S. Appl. No. 15/093,075, filed Apr. 7, 2016, Soh et al.
PCT International Search Report and Written Opinion for PCT/US2016/064608 dated Apr. 18, 2017.
All Final and Non-Final Office Actions for U.S. Appl. No. 14/677,578, P&G Case 13769.
All Final and Non-Final Office Actions for U.S. Appl. No. 14/677,636, P&G Case 13770.
All Final and Non-Final Office Actions for U.S. Appl. No. 14/742,145, P&G Case 13356M.
All Final and Non-Final Office Actions for U.S. Appl. No. 14/755,567, P&G Case 13461M.
All Final and Non-Final Office Actions for U.S. Appl. No. 14/959,234, P&G Case 13640M.
All Final and Non-Final Office Actions for U.S. Appl. No. 14/959,243, P&G Case 13641M.
All Final and Non-Final Office Actions for U.S. Appl. No. 15/093,075, P&G Case AA1008.
All Final and Non-Final Office Actions for U.S. Appl. No. 15/367,356, P&G Case 14116.
All Final and Non-Final Office Actions for U.S. Appl. No. 15/367,363, P&G Case 14117.
All Final and Non-Final Office Actions for U.S. Appl. No. 15/367,369, P&G Case 14118.
Anonymous: "Spotlight on Apricot Oil, Black Girl with Long Hair", Apr. 5, 2013, Retrieved from the internet: URL: http://blackgirllonghair.com/2013/04/spotlight-on-apricot-oil/, Retrieved Jun. 2, 2016.
John Frieda Frizzease conditioner product (John Frieda, Frizzease smooth start conditioner—https://www.johnfrieda.com/en-UK/products/frizz-ease/smooth-start-conditioner.html, last visit date: Jan. 17, 2018 (year 2018).
Khan, H., "5 ways to straighten your hair without heat", Hair Beauty Tips, Jul. 12, 2013, pp. 1-4.
Medline Plus "Aging changes in hair and nails", US National Library of Medicine, Oct. 27, 2014, pp. 1-3.

(56) References Cited

OTHER PUBLICATIONS

PCT International Search Report and Written Opinion for PCT/US2015/036195 dated Dec. 16, 2015.
PCT International Search Report and Written Opinion for PCT/US2016/025827 dated Jun. 24, 2016.
PCT International Search Report and Written Opinion for PCT/US2016/064604 dated Apr. 10, 2017.
PCT International Search Report and Written Opinion for PCT/US2016/064606 dated Apr. 12, 2017.
PCT Invitation to Pay Additional Fees and, Where Applicable, Protest Fee for PCT/US2015/064608 dated Feb. 20, 2017, 9 pages.
PCT Invitation to Pay Additional Fees and, Where Applicable, Protest Fee for PCT/US2016/064604 dated Feb. 15, 2017, 10 pages.
PCT Invitation to Pay Additional Fees and, Where Applicable, Protest Fee for PCT/US2016/064606 dated Feb. 20, 2017, 14 pages.
All Final and Non-Final Office Actions for U.S. Appl. No. 15/949,539, P&G Case 14768.
All Final and Non-Final Office Actions for U.S. Appl. No. 15/949,555, P&G Case 14769.
U.S. Appl. No. 15/949,539, filed Apr. 10, 2018, Punyani.
U.S. Appl. No. 15/949,555, filed Apr. 10, 2018, Punyani.

* cited by examiner

COMPOSITION FOR HAIR FRIZZ REDUCTION

FIELD OF THE INVENTION

The present invention relates to a leave-on composition comprising one or more materials useful for treating hair frizz.

BACKGROUND OF THE INVENTION

Hair frizz is described by consumers as the appearance of unruly fibers at the top of the scalp and tips of hair as well as an increased volume through the bulk of the hair. Generally they see this frizz on days when there is humid weather and the level of moisture in the air is high. The appearance of frizz is undesired and it is often associated with a loss of shine and smoothness. The appearance of frizz and loss of shine and smoothness are associated with a perception of poor hair health. The basic mechanism causing frizz in high humid environments is that at high humidity water penetrates into hair and changes the chemical bond interactions inside the hair. During styling, the consumer will create a 'wet set' where hair is blow dried or flat ironed to create the desired shape. During drying, water is evaporated from hair and hydrogen bonds are formed between the protein peptide chains holding the style in place. As moisture diffuses into hair the hydrogen bonds are broken and hair returns back to its natural shape. For consumers who straighten their hair by blow drying or flat ironing this return to a curled style is associated with a loss of alignment and increased volume. In addition, at high moisture levels in hair the fiber diameter increases which also increases the overall volume of hair.

The typical strategy to prevent frizz is to formulate leave-on products with surface-depositing materials such as silicone, oils, conditioning silicone etc. which make hair more hydrophobic and decrease inter-fiber interactions. At high levels these materials can also provide increased cohesive forces holding fibers together to prevent frizz from occurring. With these materials depositing on the hair surface a greasy look and feel is typically experienced, which is an undesired trade-off of frizz reduction.

Consequently, a need exists for a treatment product that combines effective frizz control with additional hair benefits that the consumer can notice and feel and, at the same time, is delightful to use without having a sticky or greasy feel.

SUMMARY OF THE INVENTION

The present invention is direct to an aqueous hair leave-on composition for hair frizz reduction comprising:

from about 0.15% to about 12.0% of a moisture control material or mixture of moisture control materials wherein the moisture control material is selected from one or more of the following classes:

1) Class I having the structure selected from:

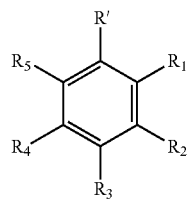

wherein R' is —COOY, sulfonic acid, or —C=CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH=CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0.

Without being bound by theory, the materials in the leave-on treatment composition of the present invention provide excellent frizz performance without a negatively affecting hair feel. These materials prevent water uptake into hair under high humidity conditions, reducing the negative impact of frizz. By providing frizz benefits by penetrating the hair fiber as opposed to depositing on the hair surface, the frizz benefit is not associated by negative hair feel, which is typically observed with current commercial anti-frizz products. These and additional features provided by the embodiments of the present invention will be more fully understood in view of the following detailed description.

DETAILED DESCRIPTION OF EMBODIMENTS OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity (RH), unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application" as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

"Leave-on," in reference to compositions, means compositions intended to be applied to and allowed to remain on the keratinous tissue. These leave-on compositions are to be distinguished from compositions, which are applied to the hair and subsequently (in a few minutes or less) removed either by washing, rinsing, wiping, or the like. Leave-on compositions exclude rinse-off applications such as shampoos, rinse-off conditioners, facial cleansers, hand cleansers, body wash, or body cleansers. The leave-on compositions may be substantially free of cleansing or detersive surfactants. For example, "leave-on compositions" may be left on the keratinous tissue for at least 15 minutes. For example, leave-on compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

"Soluble" means at least about 0.1 g of solute dissolves in 100 ml of solvent, at 25° C. and 1 atm of pressure.

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. The weight average molecular weight may be measured by gel permeation chromatography. "QS" means sufficient quantity for 100%.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. Polymers made from two or more different types of monomers are called copolymers. The distribution of the different monomers can be calculated statistically or block-wise—both possibilities are suitable for the present invention. Except if stated otherwise, the term "polymer" used herein includes any type of polymer including homopolymers and copolymers.

The mechanism of action for frizz generation involves moisture from the environment being absorbed by hair and occupying hydrogen bonding sites within hair, including those on the peptide backbone and also associated with acidic and basic side chains of amino acid residues such as lysine, arginine and glutamic acid. This internal water replaces hydrogen bonds that had been created during styling that hold hair in a desired configuration. As a consequence, hair returns to its natural shape which typically leads to unwanted wave, loss of alignment and frizz. In addition, uptake of water by these hydrogen bonding sites swells the hair fiber causing style expansion, which is another indicator of frizz. Without being bound by theory, the materials covered by this invention will replace water at the hydrogen bond sites inside hair and prevent water uptake. Reduction of water inside hair will lead to a reduction in the appearance of frizz under high humidity conditions. Because the mechanism of action is related to the space inside the hair fibers, there are no feel negatives, such as, for example, greasy or oily feel associated with the benefit. The reduction in water uptake is measured using Dynamic Vapor Sorption (DVS) method, which measures a weight increase of hair equilibrated at 0% Relative Humidity (RH) versus 90% RH. Significant frizz benefit is measured on hair treated by materials that caused a reduction in water uptake of higher than 5% versus control hair that is not treated with such materials. The treatment involved the application of a 2% w/w solution of the material in 50:50 water:ethanol solvent.

Preferred materials include salicylic acid, 2,3-dihydroxybenzoic acid, 2,6-dihydroxybenzoic acid, 3-aminobenzoic acid, gallic acid, ethyl gallate, 5-chlorosalicylic acid, trans-ferulic acid, p-coumaric acid, ricinoleic acid, isovaleric acid, isobutyric acid, 2-hexyl-1-decanol, phytol and sorbitan caprylate. These materials are chosen from Molecular Class I and/or Molecular Class II or can also be used in combination to increase the size of the benefit.

In an embodiment of the present invention, the concentration of the Moisture Control Material or the concentration of the mixture of Moisture Control Material in a hair leave-on composition is from about 0.15% to about 12%, in an embodiment from about 0.2% to about 5%, in a further embodiment from about 0.5% to about 4%, and in yet a further embodiment from about 1.0% to about 3.0%.

Molecular Class I: Polar, acidic compounds with the following properties: Protein Binding (PB) > 20 AND Molecular Volume (Mol. Vol). < 500 AND logP < 3 AND Hydrogen-binding (H-binding) > 10 AND pKa < 5.0, wherein PB is % protein binding, Mol. Vol is molecular volume (in Å$^3$); log P is n-octanol/water partition coefficients. These properties can be calculated using Volsurf software (http://www.moldiscovery.com/soft_volsurf.php). H-bond is the energy from hydrogen bonds between molecules from Hansen Solubility Parameters and pKa value is a logarithmic measure of the acid dissociation constant.

| Name (1% wt/vol) | PB | Mol. Vol. | log P | pKa | H-bond (MPa 1/2) | % Water Reduction |
|---|---|---|---|---|---|---|
| 2,4-Dihydroxybenzoic acid | 28 | 324 | 1.5 | 3.2 | 23 | 30 |
| 3-Hydroxybenzoic Acid | 38 | 314 | 1.6 | 4.3 | 20 | 20 |
| Gallic acid | 23 | 337 | 0.9 | 4.4 | 23 | 15 |
| 3-Aminobenzoic acid | 41 | 326 | 0.9 | 3.6 | 16 | 12 |
| 4-Aminobenzoic acid | 42 | 323 | 0.9 | 3.5 | 16 | 12 |
| 2,5-Dihydroxybenzoic acid | 31 | 329 | 1.6 | 2.9 | 23 | 27 |
| 3,4-Dihydroxybenzoic acid | 27 | 327 | 0.9 | 4.4 | 23 | 20 |
| 3,5-Dihydroxybenzoic acid | 27 | 327 | 0.9 | 4.1 | 23 | 15 |
| 2,6-Dihydroxybenzoic acid | 37 | 326 | 1.6 | 2.1 | 23 | 35 |
| 5-Chlorosalicylic acid | 56 | 361 | 2.3 | 3.0 | 21 | 28 |
| Salicylic acid | 44 | 320 | 2.1 | 3.1 | 20 | 18 |
| Trans-Ferulic Acid | 50 | 451 | 1.5 | 4.5 | 19 | 6 |
| p-Coumaric acid | 46 | 391 | 1.6 | 4.5 | 20 | 8.8 |
| 4-Hydroxybenzenesulphonic acid | 55 | 271 | 1.5 | 2.7 | 22 | 26 |
| 3-Chloro-4-hydroxybenzoic acid | 49 | 356 | 2.1 | 4.1 | 20 | 11 |
| 3,5-Dichloro-4-hydroxybenzoic acid | 51 | 397 | 2.8 | 3.8 | 20 | 15 |
| 2,5 Dihydroxyterephthalic acid | 20 | 375 | 1.1 | 2.1 | 22 | 18 |
| 3-Aminophenol | 45 | 284 | 0.6 | 4 | 17 | 14 |
| 3-Hydroxyanilinium chloride | 32 | 280 | 0.6 | 4 | 17 | 16 |
| 2-Aminophenol | 49 | 288 | 1.0 | 4 | 17 | 14 |
| 4-Aminophenol | 39 | 284 | 0.6 | 4 | 17 | 10 |
| N-4-Hydroxyphenylglycine | 37 | 388 | 1.3 | 3 | 13 | 15 | b) Molecular Class II: Weakly polar to non-polar, weakly to non-acidic compounds that have the following properties: PB > 10 AND Mol. Vol. < 1500 AND log P > 0.5 AND pKa ≥ 5 AND H-binding > 4, wherein PB is % protein binding, Mol. Vol is molecular volume (in Å$^3$); logP is n-octanol/water partition coefficients. These properties can be calculated using Volsurf software (http://www.moldiscovery.com/soft_volsurf.php). H-bond is the energy from hydrogen bonds between molecules from Hansen Solubility Parameters and pKa value is a logarithmic measure of the acid dissociation constant.

| Name | PB | Mol. Vol. | logP | pKa | H-bond (MPa^1/2) | % water reduction |
|---|---|---|---|---|---|---|
| 2-Hydroxyethyl salicylate | 45 | 419 | 1.5 | 8.3 | 19.1 | 10 |
| Ethyl gallate | 43 | 431 | 1.4 | 8.7 | 22.6 | 17 |
| Oleic Acid | 100 | 832 | 7 | 5 | 6.4 | 14 |
| Ricinoleic acid | 84 | 841 | 5.9 | 5 | 17.8 | 8.8 |
| Isovaleric acid | 29 | 295 | 1.3 | 5 | 9.7 | 15 |
| Isobutyric acid | 15 | 254 | 1 | 5 | 10.4 | 5 |
| 2-Hexyl-1-decanol | 87 | 745 | 6.8 | 15 | 10.1 | 11 |
| Phytol | 100 | 874 | 8.0 | 13 | 9.6 | 14 |
| Sorbitan caprylate | 32 | 695 | 1.3 | 12 | 21.8 | 11 |
| Glyceryl monooleate | 96 | 974 | 6.27 | 12.8 | 16.2 | 5 |
| Isostearyl isostearate | 100 | 1527 | 14.7 | 14 | 4.2 | 11 |
| Ethyl linoleate | 82 | 903 | 7.71 | 7.8 | 5.1 | 8 |
| Isopropyl myristate | 97 | 798 | 6.99 | 8.8 | 5.0 | 12 |
| Octyl salicylate | 82 | 646 | 5.4 | 7.1 | 11.7 | 14 |

A Class I having the structure selected from:

1) Class I having the structure selected from:

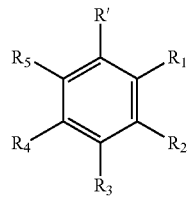

wherein R' is —COOY, sulfonic acid, or —C=CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH=CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0;

2) Class II having the structure selected from:

A)

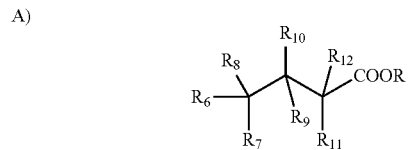

wherein R is hydrogen or metal ion, $R_6$ is methyl, ethyl, propyl, alkenyl or phenyl having less than 12 carbon atoms and wherein $R_7$, $R_8$, $R_9$, $R_{10}$, $R_{11}$, $R_{12}$ are hydrogen, methyl, ethyl, propyl, phenyl, hydroxyl, methoxy or ethoxy groups;

B)

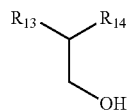

an alcohol wherein R13 is an alkyl, alkenyl, straight or branched carbon chains and; and wherein R14 is hydrogen, hydroxyl, alkyl, methyl, ethyl and propyl wherein the structure of such alcohol contains less than 20 total carbon atoms;
c) An alcohol comprising an unsaturated double bond in the C2 position. A non limiting example would be phytol.
d) an alkyl-substituted glycol wherein the structure of such alkyl substituted glycol contains less than 20 carbon atoms;
e) a monoalkyl or dialkyl substituted glycerin or mono- or di-esters of glycerin with fatty acids wherein the structure of such monoalkyl- or dialkyl-substituted glycerin or glycerin esters contains less than 20 total carbon atoms;

f)

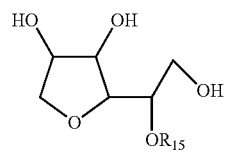

wherein $R_{15}$ could be hydrogen, alkyl, alkenyl, phenyl group and wherein the structure of the $R_{13}$ group contains less than 20 carbon atoms;
g) a fatty acid ester containing from 15-40 total carbon atoms and wherein the moisture control material of Class II is weakly to non-acidic and further wherein the moisture control material of Class II has protein binding higher than 10 and molecular volume lower than 1500 and log P higher than 0.5 and pKa of 5 or higher and hydrogen-binding higher than 4.

pH of Compositions

In an embodiment of the present invention, the table below demonstrates data of the difference of % water reduction of hair treated with leave on composition containing 1% salicylic acid in ethanol:water (50:50) at various values of pH vs control (hair treated with composition of ethanol:water (50:50). As shown in below table, at lower pH, the present invention demonstrates improved performance compared to higher pH.

| Formula Example | pH 3 | pH 4.2 | pH 7 | pH 10 |
|---|---|---|---|---|
| Raw Material | | | | |
| Distilled Water | QS | QS | QS | QS |
| Ethanol | 50.0 | 50.0 | 50.0 | 50.0 |
| Salicylic acid | 1.0 | 1.0 | 1.0 | 1.0 |
| Final pH | 3.2 | 4.2 | 7 | 10 |
| % Water Reduction | 30 | 27 | 22 | 15 |

In an embodiment of the present invention, the pH of a composition of the present invention comprising material from Molecular Class I may be in the range of from about 1 to about 9, in another embodiment a pH of from about 2 to about 7, in a further embodiment a pH of from about 4 to about 5.5.

In an embodiment of the present invention, the pH of a composition of the present invention comprising materials from Molecular Class II may be in the range of from about 1 to about 9, in another embodiment a pH of from about 2 to about 8, and in a further embodiment a pH of from about 3 to about 7.

In an embodiment of the present invention, the Moisture control Material is a carboxylic acid ester. In an embodiment, the carboxylic acid ester is based on a fatty acid wherein the molecule of the fatty acid comprises of more than 14 carbon atoms. Non-limiting examples of such esters are isostearyl isostearate, methyl stearate, methyl palmitate, and methyl oleate. In another embodiment of the present invention, the carboxylic acid ester is part of a mixture of materials prepared via the reaction of natural oils using methanol. Non-limiting examples of such mixture is the mixture that is produced by the product of the reaction of refined palm kernel oil with methanol, followed by fractionation via distillation. A commercial product that meets this description is the Heavy Cut Ester CE-1875 (supplied by P&G Chemicals with CAS Number 6772-38-3) containing ingredients such as methyl stearate, methyl palmitate, methyl oleate as major ingredients, as well as methyl laurate, methyl myristate, methyl behenate and other materials as minor ingredients.

FORMULATIONS AND EXAMPLES

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

Examples

Leave-on Treatment Composition Preparation

The leave-on treatment compositions are prepared by adding the Moisture Control Materials and perfume, if needed, into a 50:50 ethanol/water carrier and stirred until complete dissolution. The solution pH is adjusted using sodium hydroxide (50% w/w) to a final pH of 4.0-4.2. The Sepigel 305 is then added, if needed, and the solution is mixed using a high-speed-mixer for 2-5 minutes at 1800-2300 rpm until a uniform composition is obtained.

Leave-on Hair Treatment Protocol:

An amount of 0.20 g of each composition of Examples I to IV is spread via a syringe onto separate natural virgin brown hair switches weighing 2.0 g (dosage 0.10 g of solution per g of hair). The hair is allowed to air dry and then analyzed using the DVS method described above. The experiment is repeated for a dosage of 0.50 g of solution per g of hair. The hair in this case is also assessed by expert graders, as described below, in addition to the DVS analysis.

DVS Measurement:

An amount of 25-30 mg of hair with length of approximately 1 cm is weighed and hold for equilibration at 0% RH for 16 hours. After the 16-hour period, the RH is increased to 10% and maintained at this level for 6 hours. Then, the RH is increased by 10% after every 6 hours interval until it reaches 90% RH. The % water reduction is calculated as follows:

A=Amount of water absorbed by the hair treated with composition containing the Moisture Control Material B=Amount of water absorbed by the hair treated with control composition (only carrier) containing no Moisture Control Material % Water reduction=$[(B-A)\times100]/B$ Hair Switch Feel Assessment Method: The treated hair switches are kept at high humidity (above 85% RH) for 2 hrs and then ten expert graders are asked to rate each of them in terms of tactile feel based on a 5 point scale, 5 being the highest (best feel) and 1 being the lowest rating.

Leave-on Treatment Formulation:

| | Formula Example | | | | | | | |
|---|---|---|---|---|---|---|---|---|
| | Leave-on treatment Control (wt./wt.)% | I (wt./wt.)% | II (wt./wt.)% | III (wt./wt.)% | IV (wt./wt.)% | V (wt./wt.)% | VI (wt./wt.)% | VII (wt./wt.)% |
| Raw Material | | | | | | | | |
| Distilled Water | QS | QS | QS | QS | QS | QS | QS | QS |
| Ethanol | 50.00 | 50.00 | 50.00 | 50.00 | 50.00 | 50.00 | 50.00 | 50.00 |
| Polyacrylamide & C13-14 Isoparaffin & Laureth-7 (Sepigel 305) | 1.85 | 1.85 | 1.85 | 1.85 | 1.85 | 1.85 | 1.85 | 1.85 |
| Perfume | 0.46 | 0.46 | 0.46 | 0.46 | 0.46 | 0.46 | 0.46 | 0.46 |
| Salicylic acid | 0 | 2.0 | 0 | 0 | 2.0 | 2.0 | 0.0 | 0.0 |
| 5-Chlorosalicylic acid | 0 | 0 | 2.0 | 0 | 0 | 0 | 2.0 | 2.0 |
| 2,4-Dihydroxybenzoic acid | 0 | 0 | 0 | 2.0 | 0.15 | 0.15 | 0.15 | 0.15 |
| Oleic acid | 0 | 0 | 0 | 0 | 0 | 0.25 | 0 | 0.25 |
| 2-Hexyl-1-decanol | 0 | 0 | 0 | 0 | 0 | 0.25 | 0 | 0.25 |
| Final pH | 4.2 | 4.2 | 4.2 | 4.2 | 4.2 | 4.2 | 4.2 | 4.2 |
| % Water Reduction versus Leave-on Treatment Control at dose of 0.10 g of composition for 1.0 g of hair | '— | — | — | — | 4 | 5 | 5 | 7 |
| % Water Reduction versus Leave-on Treatment Control at | — | 4 | 5 | 5 | 9 | 8 | 10 | 10 |

-continued

| | Formula Example | | | | | | | |
|---|---|---|---|---|---|---|---|---|
| | Leave-on treatment Control (wt./wt.)% | I (wt./wt.)% | II (wt./wt.)% | III (wt./wt.)% | IV (wt./wt.)% | V (wt./wt.)% | VI (wt./wt.)% | VII (wt./wt.)% |
| dose of 0.50 g of composition for 1.0 g of hair. Control is dosed at 0.50 g of composition for 1.0 g of hair | | | | | | | | |
| Feel Rating Leave-on Treatment Control at dose of 0.10 g of composition for 1.0 g of hair | 1 | 1 | 2 | 2 | 2 | 3 | 2 | 4 |

| Formula Example | VIII | IX | X | XI | XII | XIII |
|---|---|---|---|---|---|---|
| Raw Material | | | | | | |
| Distilled Water | QS | QS | QS | QS | QS | QS |
| Ethanol | 50.0 | 50.0 | 50.0 | 50.0 | 50.0 | 50.0 |
| 5-Chlorosalicylic acid | 1.0 | | | 1.0 | 1.0 | 1.0 |
| 2-Hexyl-1-decanol | | | 5.0 | 5.0 | | 5.0 |
| Isostearyl isostearate | | 2.0 | | | 2.0 | 2.0 |
| Final pH | 4 | 4 | 4 | 4 | 4 | 4 |
| % Water Reduction versus Leave-on Treatment Control at dose of 0.10 g of composition for 1.0 g of hair | 1.3 | 0.7 | 1.0 | 2.0 | 1.4 | 3.0 |
| Feel Rating (on 5 scale point with 5 as highest and 1 as lowest) | 1 | 2 | 2 | 3 | 3 | 4 |

Results: Formula I to XIII showed % water reduction at high humidity. Higher % water reductions are observed in hair treated with higher doses of leave-on Formulas I-XIII.

The feel assessment results indicate that combinations of
(a) 5-Chlorosalicylic acid and 2-hexyl-1-decanol;
(b) 5-Chlorosalicylic acid and isostearyl isostearate;
(c) 5-Chlorosalicylic acid and 2-hexyl-1-decanol and isostearyl isostearate provide, not only water absorption reduction (resulting in frizz benefit), but also tactile feel benefit. This is shown by the feel comparisons of (a) Example XI versus Examples VIII and IX, (b) Example XII versus Examples VIII and X, and (c) Example XIII versus Examples VIII, IX and X.

Additional Evaluations

Additional leave-on treatment compositions are prepared (Tables 1 and 2) according to the procedure described above, which are used to treat hair switches using the procedure described above (amount of 0.10 g of composition per g of hair). The switch is kept at high humidity (above 85%) for 2 hours. Then, ten experts are asked to rate each hair switch in terms of frizz, clean feel, and greasy feel, based on a 5 point scale, 5 being the highest and 1 being the lowest rating. Acceptable values are:

For frizz, less than 2 (lower number corresponds to less frizz);

For no greasy feel less than 3, (lower number corresponds to less greasy feel), and For clean feel greater than 3 (higher number corresponds to cleaner feel).

TABLE 1

| | Class I Compounds | | | | | |
|---|---|---|---|---|---|---|
| Formula Example | Control | XIV | XV | XVI | XVII | XVIII |
| Raw Material | | | | | | |
| Distilled Water | 50.0% | 49.5% | 49.5% | 49.5% | 49.5% | 49.5% |
| Ethanol | 50.0% | 49.5% | 49.5% | 49.5% | 49.5% | 49.5% |
| 5-Chlorosalicylic acid | 0% | 1% | 0% | 0% | 0% | 0% |
| Salicylic acid | 0% | 0% | 1% | 0% | 0% | 0% |
| 4-Hydroxybenzenesulphonic acid | 0% | 0% | 0% | 1% | 0% | 0% |
| 2,4-Dihydroxybenzoic acid | 0% | 0% | 0% | 0% | 1% | 0% |
| Terminal Amino Silicone | 0% | 0% | 0% | 0% | 0% | 1% |
| Composition pH adjusted to | 4.2 | 4.2 | 4.2 | 4.2 | 4.2 | 4.2 |
| Greasy Feel | 2 | 1 | 2 | 2 | 2 | 4 |
| Frizz | 4 | 2 | 1 | 2 | 2 | 3 |
| Clean Feel | 4 | 4 | 3 | 4 | 4 | 1 |

Results of Hair Switch Rating from Class I Molecules: Molecules (5-chlorosalicylic acid, salicylic acid, 4-hydroxybenzenesulphonic acid, 2,4-dihydroxybenzoic acid) from Class I provide hair benefits. More specifically, Table 1 shows that hair treatments with 5-chlorosalicyclic acid, salicylic acid, 4-hydroxybenzenesulfonic acid and 2,4-dihydroxybenzoic acid provide frizz protection with clean feel and without greasy feel negative, as opposed to treatment with terminal aminosilicone, which provide some frizz benefit but with greasy feel negative and significantly less clean feel.

TABLE 2

Class II Compounds

| Formula Example | Control | XIX | XX | XXI | XXII | XXIII |
|---|---|---|---|---|---|---|
| Raw Material | | | | | | |
| Distilled Water | 50.0% | 49.5% | 49.5% | 49.5% | 49.5% | 49.5% |
| Ethanol | 50.0% | 49.5% | 49.5% | 49.5% | 49.5% | 49.5% |
| Isostearyl isostearate | 0% | 1% | 0% | 0% | 0% | 0% |
| 2-Hydroxyethyl salicylate | 0% | 0% | 1% | 0% | 0% | 0% |
| Octyl salicylate | 0% | 0% | 0% | 1% | 0% | 0% |
| 2-Hexyl-1-decanol | 0% | 0% | 0% | 0% | 1% | 0% |
| Terminal Amino Silicone | 0% | 0% | 0% | 0% | 0% | 1% |
| Composition pH adjusted to | 4.2 | 4.2 | 4.2 | 4.2 | 4.2 | 4.2 |
| Greasy Feel | 2 | 2 | 2 | 2 | 3 | 4 |
| Frizz | 4 | 2 | 2 | 1 | 1 | 3 |
| Clean Feel | 4 | 3 | 3 | 3 | 3 | 1 |

Results of Hair Switch Rating from Class II Molecules: Molecules (Isostearyl isostearate, 2-hydroxyethyl salicylate, octyl salicylate, 2-hexyl-1-decanol) from Class II provide hair benefits. More specifically, Table 2 shows that hair treatment with isostearyl isostearate, 2-hydroxyethyl salicylate, octyl salicylate, and 3-hexyl-1-decanol provide frizz protection with clean feel and without greasy feel negative, as opposed to treatment with terminal aminosilicone, which provide some frizz benefit with greasy feel negative and significantly less clean feel.

Evaluation of Hair Friction

Leave-on formulation containing Moisture Control Material and Silicone oil shows improvement in dry feel compared to untreated hair. This is concluded by measurement of dry hair friction. For this evaluation, natural virgin brown hair switches (4.0 g) are washed with clarifying shampoo, and then treated with leave-on treatment of composition XXIV according to the protocol described above. Before the evaluation, the switches are air dried overnight in a controlled temperature and humidity room (22° C./50% RH). The friction force (grams) between the hair surface and a urethane pad along the hair is measured, with three measurements per switch using an Instron Tester instrument (Instron 5542, Instron, Inc, Canton, Mass., USA).

TABLE 3

Hair Friction

| Formula Example | XXIV | Control Hair—No Treatment |
|---|---|---|
| Raw Material | | |
| Distilled Water | 49.5% | |
| Ethanol | 49.5% | |
| 2,4 dihydroxybenzoic acid | 1% | |
| Silicone oil | 0% | |
| Composition pH adjusted to | 4.2 | |
| Average Force (g) | 40 | 55 |

As Table 3 indicates, treatment of hair with leave-on composition containing Moisture Control material and silicone oil results in reduced hair friction, which indicates improved dry feel.

It is known that organic hydrophobic molecules that are naturally present inside the hair (e.g. as part of Cell Membrane Complex lipids) contribute to its strength and integrity. It is also known that cosmetic treatments, such as oxidative coloring and permanent shaping result in reduction of the concentration of such hydrophobic material from hair Thus, penetration of hydrophobic materials (e.g. Class II materials) inside the hair can contribute to lipid replenishment, which, at the same time, reduces water uptake to deliver moisture or frizz control benefit. Combination of different Class II materials e.g. benzyl alcohol, 2-hexyl-1-decanol, isostearyl isostearate, have multi-functionality of penetration, getting embedded into lipid of hair and also increasing the penetration of other hydrophobic materials like oleic resulting in further increase hydrophobicity of the hair interior.

Leave On Treatment Composition Having a Gel Matrix

The leave-on treatment composition may comprise a gel matrix comprising (1) one or more high melting point fatty compounds, (2) a cationic surfactant system, and (3) an aqueous carrier.

A. Cationic Surfactant System

The gel matrix of the leave-on composition includes a cationic surfactant system. The cationic surfactant system can be one cationic surfactant or a mixture of two or more cationic surfactants. Preferably, the cationic surfactant is selected from mono-long alkyl quaternized ammonium salt, di-long alkyl quaternized ammonium salt, mono-long alkyl amidoamine salt or mixtures thereof. The cationic surfactant system can be included in the composition at a level by weight of from about 0.1% to about 10%, from about 0.5% to about 8%, from about 0.8% to about 5%, and from about 1.0% to about 4%.

The mono-long alkyl quaternized ammonium salt cationic surfactants useful herein are those having one long alkyl chain which has from about 12 to about 30 carbon atoms, preferably from 16 to 24 carbon atoms, more preferably 18 to 22 carbon atoms. The remaining groups attached to the nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. The counterion is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Nonlimiting examples of such mono-long alkyl quaternized ammonium salt cationic surfactants include: behenyl trimethyl ammonium salt.

The di-long alkyl quaternized ammonium salt cationic surfactants useful herein are those having two long alkyl chains of from 12 to 30 carbon atoms, more preferably from 16 to 24 carbon atoms, still more preferably from 16 to 22 carbon atoms or an aromatic, alkoxy, polyoxyalkylene, alkylamido, hydroxyalkyl, aryl or alkylaryl group having up to about 30 carbon atoms. The remaining substituents on the nitrogen atom are selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms. The counterion is a salt forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Nonlimiting examples of di-long alkyl cationic surfactants include dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide.

High Melting Point Fatty Compound

The high melting point fatty compound can be included in the composition at a level of from about 0.5%, preferably from about 1.0%, more preferably form about 1.5%, still more preferably from about 2%, even more preferably from about 4%, and to about 15%, preferably to about 10% by weight of the composition, in view of providing the benefits of the present invention. The high melting point fatty compound useful herein have a melting point of 25° C. or higher, preferably 40° C. or higher, more preferably 45° C. or higher, still more preferably 50° C. or higher. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

Aqueous Carrier

The conditioner gel matrix of the leave-on treatment composition includes an aqueous carrier which can be water or a mixture of water and water-miscible solvents.

Leave On Composition Containing Gel Matrix Preparation:

A non-limiting example of leave on formulation compositions can be prepared by any conventional method well known in the art containing gel matrix. The cationic surfactants and the fatty alcohols are mixed together and heated to from about 66° C. to about 85° C. to form an oil phase. Separately, the disodium EDTA, the Methylchloroisothiazolinone (preservative) and the water are mixed and heated to from about 20° C. to about 48° C. to form an aqueous phase. The oil phase is mixed into the water phase under high shear to form the gel matrix. The remaining of the components are added into the gel matrix with agitation. Then, the composition is cooled down to room temperature.

TABLE 4

Moisture control materials in leave on formulation containing Gel Matrix

| Formula Example | Active % | XIV (wt./wt.) % | XV (wt./wt.) % |
|---|---|---|---|
| Raw Material | | | |
| Hydroxyethyl cellulose[1] | 80 | 0.400 | 0.400 |
| Cetyl Alcohol[2] | 90 | 0.575 | 0.575 |
| Stearyl Alcohol[3] | 97 | 0.383 | 0.383 |
| Benzyl Alcohol[4] | 99 | 0.400 | 0.400 |
| Disodium EDTA, Dihydrate[5] | 99 | 0.127 | 0.127 |
| Glyceryl monostearate (PoloxWSR N-10)[6] | 1.5 | 0.299 | 0.299 |
| Terminal Amino Silicone[7] | 90-100 | 2 | 2 |
| Perfume | | 0.550 | 0.550 |
| Salicylic acid[8] | 99.5 | 0 | 2.0 |
| Isostearyl Isostearate[11] | 100 | 0 | 1.0 |
| 2-hexyldecanol[12] | 97 | 0 | 5.0 |
| Purified Water | | Q.S. | Q.S. |
| % Water Reduction versus XIV (control) at dose of 0.1 g of composition for 1 g of hair | | — | 4 |

TABLE 4-continued

Moisture control materials in leave on formulation containing Gel Matrix

| Formula Example | Active % | XIV (wt./wt.) % | XV (wt./wt.) % |
|---|---|---|---|
| pH | | 5.2 | 5.2 |
| % Frizz Reduction | | | 20 |

[1]Natrosol™ hydroxyethylcellulose Supplied by Ashland (Kentucky, US)
[2]Supplied by P&G Chemicals
[3]Supplied by P&G Chemicals
[4]Supplied by Ineos Maastricht BV (Maastricht NL)
[5]Trilon BD Powder supplied by BASF SE (Ludwigshafen, DE)
[6]POLYOX™ WSR N-10 (Glyceryl monostearate) supplied by Dow chemicals (Michigan US)
[7]Y-14945 supplied by Momentive Performance Materials
[8]Supplied by API Corpotration
[9]Supplied by Sigma Aldrich
[10]Supplied by Sigma Aldrich
[11]Crodamol ISIS supplied by Croda
[12]Isofol 16 supplied by Sasol (Brunsbuettel, DE)

Results: Hair Switches treated with leave on treatment of example XV, using the leave on hair treatment protocol described in page 12, shows % water reduction by DVS method of 4% vs hair treated with example XIV control.

Rheology Modifier

In one embodiment, the leave-on hair care composition comprises a rheology modifier to increase the substantivity and stability of the composition. Any suitable rheology modifier can be used. In an embodiment, the leave-on hair care composition may comprise from about 0.05% to about 10% of a rheology modifier, in a further embodiment, from about 0.1% to about 10% of a rheology modifier, in yet a further embodiment, from about 0.5% to about 2% of a rheology modifier, in a further embodiment, from about 0.7% to about 2% of a rheology modifier, and in a further embodiment from about 1% to about 1.5% of a rheology modifier. In an embodiment, the rheology modifier may be a polyacrylamide thickener. In an embodiment, the rheology modifier may be a polymeric rheology modifier.

In one embodiment, the leave-on hair care composition may comprise rheology modifiers that are homopolymers based on acrylic acid, methacrylic acid or other related derivatives, non-limiting examples include polyacrylate, polymethacrylate, polyethylacrylate, and polyacrylamide.

In another embodiment, the rheology modifiers may be alkali swellable and hydrophobically-modified alkali swellable acrylic copolymers or methacrylate copolymers non-limiting examples include acrylic acid/acrylonitrogen copolymer, acrylates/steareth-20 itaconate copolymer, acrylates/ceteth-20 itaconate copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/vinylneodecanoate crosspolymer, and acrylates/C10-C30 alkyl acrylate crosspolymer.

In a further embodiment, the rheology modifiers may be crosslinked acrylic polymers, a non-limiting example includes carbomers.

In a father embodiment, the rheology modifiers may be alginic acid-based materials; non-limiting examples include sodium alginate, and alginic acid propylene glycol esters.

In a further embodiment, the rheology modifier may be an associative polymeric thickeners, non-limiting examples include: Hydrophobically modified cellulose derivatives; Hydrophobically modified alkoxylated urethane polymers, nonlimiting example include PEG-150/decyl alcohol/SMDI copolymer, PEG-150/stearyl alcohol/SMDI copolymer, polyurethane-39; Hydrophobically modified, alkali swellable emulsions, non-limiting examples include hydrophobically modified polyacrylates, hydrophobically modified polyacrylic acids, and hydrophobically modified polyacrylamides; hydrophobically modified polyethers wherein these materials may have a hydrophobe that can be selected from cetyl, stearyl, oleayl, and combinations thereof, and a hydrophilic portion of repeating ethylene oxide groups with repeat units from 10-300, in another embodiment from 30-200, in a further embodiment from 40-150. Non-limiting examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

In a further embodiment, the rheology modifier may be cellulose and derivatives; nonlimiting examples include microcrystalline cellulose, carboxymethylcelluloses, hydroxyethylcellulose, hydroxypropylcellulose, hydroxypropylmethylcellulose, methylcellulose, ethylcellulose, nitro cellulose, cellulose sulfate, cellulose powder, and hydrophobically modified celluloses.

In an embodiment, the rheology modifier may be a guar and guar derivatives; nonlimiting examples include hydroxypropyl guar, and hydroxypropyl guar hydroxypropyl trimonium chloride.

In an embodiment, the rheology modifier may be polyethylene oxide, polypropylene oxide, and POE-PPO copolymers.

In an embodiment, the rheology modifier may be polyvinylpyrrolidone, crosslinked polyvinylpyrrolidone and derivatives. In a further embodiment, the rheology modifier may be polyvinyalcohol and derivatives.

In a further embodiment, the rheology modifier may be polyethyleneimine and derivatives.

In another embodiment, the rheology modifier may be silicas; nonlimiting examples include fumed silica, precipitated silica, and silicone-surface treated silica.

In an embodiment, the rheology modifier may be water-swellable clays non-limiting examples include laponite, bentolite, montmorilonite, smectite, and hectonite.

In an embodiment, the rheology modifier may be gums nonlimiting examples include xanthan gum, guar gum, hydroxypropyl guar gum, Arabia gum, tragacanth, galactan, carob gum, karaya gum, and locust bean gum.

In a further embodiment, the rheology modifier may be, dibenzylidene sorbitol, karaggenan, pectin, agar, quince seed (*Cydonia oblonga* Mill), starch (from rice, corn, potato, wheat, etc), starch-derivatives (e.g. carboxymethyl starch, methylhydroxypropyl starch), algae extracts, dextran, succinoglucan, and pulleran, Non-limiting examples of rheology modifiers include acrylamide/ammonium acrylate copolymer (and) polyisobutene (and) polysorbate 20, acrylamide/sodium acryloyldimethyl taurate copolymer/isohexadecane/polysorbate 80, acrylates copolymer; acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil, C12-16 alkyl PEG-2 hydroxypropylhydroxyethyl ethylcellulose (HM-EHEC), carbomer, crosslinked polyvinylpyrrolidone (PVP), dibenzylidene sorbitol, hydroxyethyl ethylcellulose (EHEC), hydroxypropyl methylcellulose (HPMC), hydroxypropyl methylcellulose (HPMC), hydroxypropylcellulose (HPC), methylcellulose (MC), methylhydroxyethyl cellulose (MEHEC), PEG-150/decyl alcohol/SMDI copolymer, PEG-150/stearyl alcohol/SMDI copolymer, polyacrylamide/C13-14 isoparaffin/laureth-7; polyacrylate 13/polyisobutene/polysorbate 20; polyacrylate crosspolymer-6, polyamide-3; polyquaternium-37 (and) hydrogenated polydecene (and) trideceth-6, polyurethane-39, sodium acrylate/acryloyldimethyltaurate/dimethylacrylamide, crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol Ulterez 30, Carbopol 1342, Sepigel™ 305, Simulgel™600, Sepimax Zen, and combinations thereof.

Carrier

According to another aspect of the present invention, the leave-on hair care compositions may further include at least about 20 weight percent of an aqueous carrier. According to one embodiment, the aqueous carrier may be prepared from demineralized or distilled water, for example. In an embodiment of the present invention, the carrier may comprise water, organic solvents (miscible or non-miscible with water), silicone solvents or a mixture thereof. In one embodiment of the present invention, a volatile carrier may include water or a mixture of water and organic solvents. In a further embodiment, the solvents may be dermatologically acceptable. In a further embodiment, the carrier may comprise water with minimal or no significant concentrations of organic solvent, except as otherwise incidentally incorporated into the composition as minor ingredients of other components. In another embodiment, water, organic and silicone solvents that have boiling points below or equal to 250° C. may be volatile solvents and volatile carriers. In one embodiment, solvents with boiling points above 250° C. may be considered non-volatile.

Non-limiting examples of a carrier may include water and solutions or mixtures of water with lower alkyl alcohols and/or polyhydric alcohols. Examples of lower alkyl alcohols are monohydric alcohols having 1 to 6 carbons such as ethanol, methanol, propanol, isopropanol, butanol, pentanol, and hexanol. Examples of polyhydric alcohols are glycols, such as dipropylene glycol, propylene glycol, butylene glycol, 1,4-butanediol, 3-allyloxy-1,2-propanediol, 1,2-hexanediol, 1,6-hexanediol, 1,3-butanediol, 1,3-propanediol, 2,2'-thiodiethanol, glycerin and other diols.

Other non-limiting examples of organic solvents include polyglycols such as polypropylene glycol, polyethylene glycol, mixture of butylene glycol, polypropylene glycol, polyethylene glycol and ethers, such as dipropylene glycol n-butyl ether, sugars, and sugar derivatives.

Penetration of Moisture Control Material Inside the Hair

In an embodiment of the present invention, compositions can comprise of glycols, polyglycols, urea, ethers or mixture thereof. These materials increase penetration of moisture control actives such as salicylic acid, 5-chloro salicylic acid, improving their performance. Propylene glycol, butylene glycol and other glycols, increase penetration of 5-chlorosalicylic acid inside hair as it acts as carrier for the actives to penetrate further. As active penetration increases, there is an increase in efficacy of the active, i.e. there is increase in % water reduction as shown below in Table 5. Table 5 shows the amount of 5-chlorosalicylic acid that penetrates inside oxidatively damaged hair after hair treatment with two different compositions. It also shows the % water reduction observed after the treatment versus treatment with control leave-on treatment compositions. These results demonstrate that 5-chlorosalicylic acid penetrates 4 times more in the presence of propylene glycol and there is an increase in % water reduction as measured by DVS of approximate 4 times more than without propylene glycol. A further non-limiting example of a material that enhances the penetration of moisture control material is 2-hydroxyethyl urea. Leave on treatment compositions that contain 2% of 2-hydroxyethyl urea increases the penetration of salicylic acid inside hair by 14% compared to the corresponding composition that does not contain 2-hydroxyethyl urea (see example XXVII and XVIII).

TABLE 5

Enhancing of hair penetration of Moisture Control Material in oxidatively damaged (bleached) Caucasian hair

| Formula Example | Control | XXV | XXVI | XXVII | XXVIII |
|---|---|---|---|---|---|
| Raw Material | | | | | |
| Distilled Water | 50.0% | 48.93% | 43.9% | 48.93% | 48.00% |
| Ethanol | 50.0% | 48.93% | 43.9% | 48.93% | 48.00% |
| 5-Chlorosalicylic acid | 0.0% | 2.0% | 2.0% | 0.0% | 0.0% |
| 2-hydroxyethyl urea | 0.0% | 0.0% | 0.0% | 0.0% | 2.0% |
| Salicylic acid | 0.0% | 0.0% | 0.0% | 2.0% | 2.0% |
| 2,4-Dihydroxybenzoic acid | 0.0% | 0.15% | 0.15% | 0.0% | 0.0% |
| Propylene glycol | 0.0% | 0% | 10% | 0% | 0.0% |
| Composition pH adjusted to | 4.2 | 4.2 | 4.2 | 4.2 | 4.2 |
| % Water Reduction versus control treatment | — | 0.67% | 3% | — | — |
| Amount of 5-chlorosalicylic acid inside the hair (mg/g of hair) | — | 1 | 3.97 | — | — |
| Amount of Salicylic acid inside hair (mg/g of hair) after 5 cycles | — | — | — | 4.7 | 5.6 |

The penetration amount of 5-chlorosalicylic acid is determined using the following protocol. Each hair tress is extracted 3 times with 0.1% TFA (Trifluoroacetic acid) in methanol and the individual extracts are analyzed separately using HPLC method.

In addition to the increase of the penetration amount of the moisture control material, the presence of glycol in the composition prevents the crystallization of part of the moisture control material in the surface of the hair Such crystallization causes a non-smooth, negative hair feel, which may be perceived by consumers as hair damage or lack of conditioning.

It has been observed that in an embodiment of the present invention the presence of propylene glycol may provide penetration enhancement for Molecular Class I and Class II materials.

Silicones

The conditioning agent of the compositions of the present invention can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat Nos.5,104,646, and 5,106,609, which descriptions are incorporated herein by reference. The silicone conditioning agents for use in the compositions of the present invention can have a viscosity, as measured at 25° C., from about 20 to about 2,000,000 centistokes ("csk"), from about 1,000 to about 1,800,000 csk, from about 50,000 to about 1,500,000 csk, and/or from about 100,000 to about 1,500,000 csk.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the embodiments of the present invention include, but are not limited to, emulsions of insoluble polysiloxanes prepared in accordance with the descriptions provided in U.S. Pat. No. 4,476,282 and U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscometer with spindle 6 at 2.5 rpm. The silicone emulsion may further include an additional emulsifier together with the anionic surfactant, Other classes of silicones suitable for use in compositions of the present invention include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

Organic Conditioning Materials

The conditioning agent of the compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Hair Health Actives

In an embodiment of the present invention, a scalp health active may be added to provide scalp benefits. This group of materials is varied and provides a wide range of benefits including anti-dandruff, anti-fungal, anti-microbial, moisturization, barrier improvement, and anti-oxidant, anti-itch, and sensates. Such skin health actives include but are not limited to: zinc pyrithione, climbazole, octopirox, vitamin E and F, salicylic acid, glycols, glycolic acid, PCA, PEGs, erythritol, glycerin, lactates, hyaluronates, allantoin and other ureas, betaines, sorbitol, glutamates, xylitols, menthol, menthyl lactate, isocyclomone, benzyl alcohol, and natural extracts/oils including peppermint, spearmint, argan, jojoba and aloe.

Anti-Dandruff Actives

In an embodiment of the present invention, the compositions may contain anti-dandruff agents. When present in these compositions, the anti-dandruff agent is typically included in an amount of about 0.01 wt. % to about 5 wt. %, based on the total weight of the personal care composition. In these compositions, the anti-dandruff particulate should be physically and chemically compatible with other ingredients of the composition, and should not otherwise unduly impair product stability, aesthetics, or performance.

Anti-dandruff agents suitable for use in personal care compositions include pyridinethione salts, azoles (e.g., ketoconazole, econazole, and elubiol), selenium sulfide, particulate sulfur, salicylic acid, and mixtures thereof. A typical anti-dandruff agent is pyridinethione salt. Personal care compositions can also include a zinc-containing layered material. An example of a zinc-containing layered material can include zinc carbonate materials. Of these, zinc carbonate and pyridinethione salts (particularly zinc pyridinethione or "ZPT) are common in the composition, and often present together.

In addition to the anti-dandruff active, compositions may also include one or more anti-fungal or anti-microbial actives in addition to the metal pyrithione salt actives. Suitable anti-microbial actives include coal tar, sulfur, charcoal, whitfield's ointment, castellani's paint, aluminum chloride, gentian violet, octopirox (piroctone olamine), ciclopirox olamine, undecylenic acid and it's metal salts, US 2011/0305778 A1 Dec. 15, 2011 potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Typical anti-microbials include itraconazole, ketoconazole, selenium sulphide and coal tar.

i. Azoles

Azole anti-microbials include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01 wt. % to about 5 wt. %, typically from about 0.1 wt. % to about 3 wt. %, and commonly from about 0.3 wt. % to about 2 wt. %, based on the total weight of the personal care product. Especially common for use herein is ketoconazole.

ii. Selenium Sulfide

Selenium sulfide is a particulate anti-dandruff agent suitable for use in anti-microbial personal care compositions, effective concentrations of which range from about 0.1 wt. % to about 4 wt. %, based on the total weight of the personal care product, typically from about 0.3 wt. % to about 2.5 wt. %, commonly from about 0.5 wt. % to about 1.5 wt. %. Selenium sulfide is generally regarded as a compound having one mole of selenium and two moles of sulfur, although it may also be a cyclic structure that conforms to the general formula Se S y, wherein x+y=8. Average particle diameters for the selenium sulfide are typically less than 15 μm, as measured by forward laser light scattering device (e.g. Malvern 3600 instrument), typically less than 10 μm. Selenium sulfide compounds are described, for example, in U.S. Pat. Nos. 2,694,668; 3,152,046; 4,089,945; and 4,885,107.

iii. Sulfur

Sulfur may also be used as a particulate anti-microbial/anti-dandruff agent in anti-microbial personal care compositions. Effective concentrations of the particulate sulfur are typically from about 1 wt. % to about 4 wt. %, based on the total weight of the personal care product, typically from about 2 wt. % to about 4 wt. %.

iv. Keratolytic Agents

In some embodiments, the personal care composition can further include one or more keratolytic agents such as salicylic acid. The personal care composition may also include a combination of anti-microbial actives. Such combinations may include octopirox and zinc pyrithione, pine tar and sulfur combinations, salicylic acid and zinc pyrithione combinations, salicylic acid and elubiol combinations, zinc pyrithione and elubiol combinations, octopirox and climbazole combinations, and salicylic acid and octopirox combinations and mixtures thereof.

II. Zinc-Containing Material, Including Zinc Carbonate

In an embodiment of the present invention, compositions may include a zinc-containing layered material. Those compositions can include about 0.001 wt. % to about 10 wt. % of the zinc-containing layered material based on the total weight of the personal care composition. In an embodiment of the present invention, a personal care composition can include a zinc-containing layered material from about 0.01 wt. % to about 7 wt. % based on the total weight of the personal care composition. In yet a further embodiment of the present invention, a personal care composition can include a zinc-containing layered material from about 0.1 wt. % to about 5 wt. %, based on the total weight of the composition. Suitable zinc-containing layered materials include those described below, including zinc carbonate materials, which are presently preferred:

Zinc-containing layered structures are those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975) Zinc-containing layered materials (ZLM's) may have zinc incorporated in the layers and/or be components of the gallery ions.

Many ZLM's occur naturally as minerals. Common examples include hydrozincite (zinc carbonate hydroxide), basic zinc carbonate, aurichalcite (zinc copper carbonate hydroxide), rosasite (copper zinc carbonate hydroxide) and many related minerals that are zinc-containing. Natural ZLM's can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLM's, which are often, but not always, synthetic, is layered doubly hydroxides, which are generally represented by the formula $[M^{2+}_{1-x}M^{3+}_{x}(OH)_2]^{x+}A^{m-}_{x/m}.nH_2O$ and some or all of the divalent ions ($M^{2+}$) would be represented as zinc ions (Crepaldi, E L, Pava, P C, Tronto, J, Valim, J B J. Colloid Interfac. Sci. 2002, 248, 429-42).

Yet another class of ZLM's can be prepared called hydroxy double salts (Morioka, H., Tagaya, H., Karasu, M, Kadokawa, J, Chiba, K Inorg. Chem. 1999, 38, 4211-6). Hydroxy double salts can be represented by the general formula $[M^{2+}_{1-x}M^{2+}_{1+x}(OH)_{3(1-y)}]^+A^{n-}_{(1=3y)/n}.nH_2O$ where the two metal ion may be different; if they are the same and represented by zinc, the formula simplifies to $[Zn_{1+x}(OH)_2]^{2x+}2x\ A^-.nH_2O$. This latter formula represents (where x=0.4) common materials such as zinc hydroxychloride and zinc hydroxynitrate. These are related to hydrozincite as well wherein a divalent anion replace the monovalent anion. These materials can also be formed in situ in a composition or in or during a production process.

These classes of ZLM's represent relatively common examples of the general category and are not intended to be limiting as to the broader scope of materials which fit this definition.

Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union US 2011/0305778 A1 Dec. 15, 2011 Ld Corp.: New York, N.Y., USA), Zinc Carbonate (Elementis Pigments: Durham, UK), and Zinc Carbonate AC (Bruggemann Chemical: Newtown Square, Pa., USA).

Basic zinc carbonate, which also maybe referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice Anti-dandruff efficacy can be dramatically increased in topical compositions by the combination of an anti-dandruff agent with an effective amount of a zinc-containing layered material, wherein the zinc-containing layered material has a specified zinc lability within a surfactant system. Zinc lability is a measure of the chemical availability of zinc ion. Soluble zinc salts that do not complex with other species in solution have a relative zinc lability, by definition, of 100%. The use of partially soluble forms of zinc salts and/or incorporation in a matrix with potential complexants generally lowers the zinc lability substantially below the defined 100% maximum.

Labile zinc is maintained by choice of an effective zinc-containing layered material or formation of an effective zinc-containing layered material in-situ by known methods.

Anti-dandruff efficacy can be dramatically increased in topical compositions by the use of polyvalent metal salts of pyrithione, such as zinc pyrithione, in combination with zinc-containing layered materials. Therefore, personal care compositions can include those containing both anti-dandruff agents and zinc-containing layered materials for topical application to provide improved benefits to the skin and scalp (e.g., improved antidandruff efficacy).

Optional Ingredients

The compositions of the present invention can also additionally comprise any suitable optional ingredients as desired. For example, the composition can optionally include other active or inactive ingredients.

The compositions may include other common hair ingredients such as other anti-dandruff actives, minoxidil, conditioning agents, and other suitable materials. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, rheology modifiers, hair conditioning agents, and surfactants.

The formulations of the present invention may be present in typical hair care compositions. They may be in the form of solutions, dispersion, emulsions, powders, talcs, encapsulated, spheres, spongers, solid dosage forms, foams, and other delivery mechanisms. The composition of the present invention may be hair tonics, leave-on hair products such as conditioners, treatment, and styling products, and any other form that may be applied to the hair.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the hair care composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of Embodiments of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An aqueous hair leave-on composition for hair frizz reduction comprising: from about 0.15% to about 12% of a moisture control material or mixture of moisture control materials, wherein the moisture control material comprises salicylic acid in combination 2,4-dihydroxybenzoic acid, and wherein the leave-on composition further comprises a material selected from the group consisting of glycols, polyglycols, 2-hydroxyethyl urea and mixture thereof.

2. An aqueous hair leave-on composition according to claim 1 wherein the concentration of the Moisture Control Material or the concentration of the mixture of Moisture Control Material is from about 0.2% to about 5%.

3. An aqueous hair leave-on composition according to claim 1 wherein the concentration of the Moisture Control Material or the concentration of the mixture of Moisture Control Material is from about 0.5% to about 4%.

4. An aqueous hair leave-on composition according to claim 1 wherein the concentration of the Moisture Control Material or the concentration of the mixture of Moisture Control Material is from about 1.0% to about 3.0%.

5. An aqueous hair leave-on composition according to claim 1 wherein the moisture control material further comprise 5-chlorosalicyic acid.

6. An aqueous hair leave-on composition according to claim 1 further comprising 5-chlorosalicylic acid and propylene glycol.

7. An aqueous hair leave-on composition according to claim 1 further comprising 5-chlorosalicylic acid and silicone.

8. An aqueous hair leave-on composition according to claim 1 comprising Salicylic acid from 0.5% to 2% in combination with 2-hydroxyethyl urea from 0.2% to 10%.

9. An aqueous hair leave-on composition according to claim 1 wherein a pH of the composition is in the range of about 2 to about 7.

10. An aqueous hair leave-on composition according to claim 1 wherein the composition further comprises materials selected from the group consisting of conditioning materials, solvents, rheology modifier, thickeners, hair health actives, anti-dandruff actives, anti-oxidants, pigments, abrasives, absorbents, biological actives, buffering agents, chelating agents, opacifying agents, pH adjusters and mixtures thereof.

11. An aqueous hair leave-on composition according to claim 10 wherein the composition further comprises a metal salt of pyrithione.

12. An aqueous hair leave-on composition according to claim 1 wherein the composition further comprises a cationic surfactant system.

13. An aqueous hair leave-on composition according to claim 1 wherein the leave on composition further comprise a gel matrix comprising:
   i. from about 0.1% to about 20% of one or more high melting point fatty compounds, by weight of said hair care composition;
   ii. from about 0.1% to about 10% a cationic surfactant system of, by weight of said hair care composition; and
   iii. at least about 20% of an aqueous carrier, by weight of said hair care composition.

14. A leave on composition according to claim 13 wherein the composition further comprises a non-ionic surfactant system.

15. An aqueous hair leave-on composition for hair frizz reduction comprising from about 0.2% to about 12% of a moisture control material or mixture of moisture control materials wherein the moisture control material is a combination of salicylic acid and 2,4-dihydroxybenzoic acid and further wherein there is about a 4% to about a 10% frizz reduction vs. a control composition without the moisture control material.

* * * * *